United States Patent [19]

Koda et al.

[11] 4,122,112
[45] Oct. 24, 1978

[54] PROCESS FOR PRODUCING POLYCARBONATE OLIGOMERS

[75] Inventors: Hiroyuki Koda, Toyonaka; Takeaki Megumi, Sakai; Hiroyuki Yoshizaki, Toyonaka, all of Japan

[73] Assignee: Mitsubishi Gas Chemical Company, Inc., Japan

[21] Appl. No.: 804,169

[22] Filed: Jun. 6, 1977

[30] Foreign Application Priority Data

Jun. 9, 1976 [JP] Japan .................................. 51-67451

[51] Int. Cl.² ...................... C08G 17/13; C08G 63/62
[52] U.S. Cl. .................................. 260/463; 260/95 C; 422/134; 526/64; 526/65; 528/196
[58] Field of Search ............ 260/463, 47 XA, 77.5 D, 260/95 C, 49

[56] References Cited

U.S. PATENT DOCUMENTS

| | | | |
|---|---|---|---|
| 3,133,044 | 5/1964 | Allen et al. | 260/47 |
| 3,646,102 | 2/1972 | Kubayashi et al. | 260/463 |
| 3,674,740 | 7/1972 | Vernaleken et al. | 260/47 XA |
| 3,974,124 | 8/1976 | Narita et al. | 260/47 XA |

*Primary Examiner*—Theodore E. Pertilla
*Attorney, Agent, or Firm*—Wenderoth, Lind & Ponack

[57] ABSTRACT

A process for producing polycarbonate oligomers by the reaction of dihydroxy compounds with phosgene, which comprises contacting a mixture of a dihydroxy compound and an aqueous alkali solution with phosgene in the presence of an organic solvent in a tubular reactor to perform a first-stage reaction, introducing the first-stage reaction mixture into a tank-type reactor equipped with a stirrer and containing the aqueous alkali solution and a solution in the organic solvent of a polycarbonate oligomer formed by the reaction of the first-stage reaction product in a second stage, and performing the second-stage reaction while stirring the reaction mixture in the tank-type reactor and maintaining it at a predetermined temperature by sufficient removal of the heat of reaction.

5 Claims, 4 Drawing Figures

PROCESS FOR PRODUCING POLYCARBONATE OLIGOMERS

BACKGROUND OF THE INVENTION

This invention relates to a process for producing polycarbonate oligomers.

As is well known, the production of polycarbonate usually comprises preparing a polycarbonate oligomer of a relatively low molecular weight as an intermediate, and polymerizing the oligomer to a polycarbonate of a high molecular weight. In the conventional production of polycarbonate oligomers, either a tubular reactor or a tank-type reactor is used.

For example, Japanese Patent Publication No. 4352/66 discloses a process for continuously producing polycarbonate oligomers using a packed column-type tubular reactor. This process has the advantage that the reaction time can be shortened as compared with a process using a tank-type reactor. However, the process of the Japanese patent publication cannot easily remove the heat of reaction, and also has the defect that because the flow of the reaction mixture does not satisfactorily reach a steady state, the reproducibility of the reaction is poor, and consequently, the quality of the polymer obtained in the subsequently polymerization satage is not constant.

Japanese Laid-Open Patent Publication No. 14297/72 also discloses a process for preparing polycarbonate ogligomers using a packed column-type tubular reactor, in which phosgene is used together with an inert gas in order to remove the heat of reaction easily. This process, however, has the defect of requiring a gas-liquid separator, and is still not free from the defect that the quality of the final polymer is not constant because of the poor reproducibility of the reaction.

Japanese Patent Publication No. 21460/71 discloses a process for producing polycarbonate oligomers using a tubular reactor having an orifice plate inserted in it. According to this process, the length-to-diameter ratio of the reaction tube must be considerably high. Moreover, since only the phosgenation reaction alone tends to proceed, the resulting oligomer has a low molecular weight and contains a large amount of the terminal —OCOCl group. Thus, the decomposition of the —O—COCl group is liable to occur in a reaction of forming a polymer by polymerizing the oligomer.

Japanese Laid-Open Patent Publication No. 116195/74 discloses a process for producing polycarbonates, which comprises separately introducing gaseous phosgene at a high speed and an alkaline aqueous solution of a dihydroxy compound at a lower speed in the absence of an organic solvent into a tubular reactor equipped with a bi-component nozzle to form a polycarbonate oligomer in it, associating the resulting aqueous reaction mixture with an organic solvent downstream of the tubular reactor, introducing the associated stream into a second tubular reactor, and polymerizing the oligomer in it. However, the removal of the heat of reaction by merely jetting out the gaseous phosgene to cause the flow of liquid is insufficient and it is also difficult to inhibit side-reactions.

The processes described above which rely on the use of tubular reactors have the defect that the heat of reaction is difficult to remove, the length-to-diameter ratio of the reaction tube must be made high, and many reactors must be installed for mass production. Processes which involve the use of tank-type reactors in order to remedy the defects associated with the tubular reactors are known. However, these processes have the defect of reduced rates of reaction. Presumably, the reduced rate of reaction is ascribable to the fact that when a tubular reactor is used, the reaction between a dihydroxy compound and phosgene takes place vigorously at the inlet of the reactor, whereas in the case of a tank-type reactor, the reaction proceeds slowly in the entire inside of the reactor. Furthermore, since the reaction is carried out slowly in the tank-type reactor, the removal of the heat of reaction is relatively easy, but on the other hand, more decomposition reactions occur, and the yield of the final product decreases.

In an attempt to prevent such a decrease in the rate of reaction in a tank-type reactor, British Patent 1,118,146 discloses a process in which the reaction is carried out in the emulsified state. However, this reaction has the defect that the decomposition of phosgene becomes rapid, and the yield of the product decreases.

It is an object of this invention to provide a novel process for producing polycarbonate oligomers, which is free from the aforementioned defects of the conventional processes for producing polycarbonate oligomers using a tubular or tank-type reactor.

SUMMARY OF THE INVENTION

This invention provides a process for producing polycarbonate oligomers by the reaction of dihydroxy compounds with phosgene, which comprises contacting a mixture of a dihydroxy compound and an aqueous alkali solution with phosgene in the presence of an organic solvent in a tubular reactor to perform a first-stage reaction, introducing the first stage reaction mixture into a tank-type reactor equipped with a stirrer and containing the aqueous alkali solution and a solution in the organic solvent of a polycarbonate oligomer formed by the reaction of the first-stage reaction product in a second stage, and performing the second-stage reaction while stirring the reaction mixture in the tank-type reactor and maintaining it at a predetermined temperature by sufficient removal of the heat of reaction.

BRIEF DESCRIPTION OF THE ACCOMPANYING DRAWINGS

FIG. 1 is a flowsheet showing one example of the practice of the process of this invention; and FIGS. 2 to 4 show examples of the structure of the outlet portion of a feed tube for introducing starting materials into a tubular reactor in order to perform a first-stage reaction by contacting a mixture of a dihydroxy compound and an aqueous alkali solution with phosgene in the presence of an organic solvent.

DETAILED DESCRIPTION OF THE INVENTION

Figure 1:
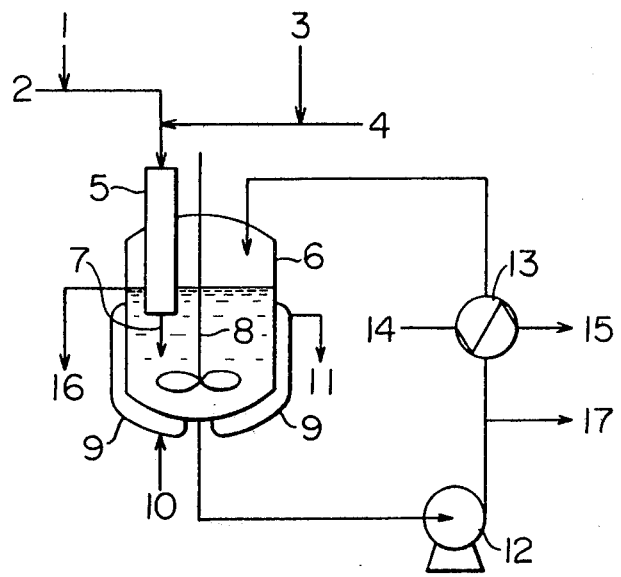

The dihydroxy compound used in this invention is at least one compound of the formula

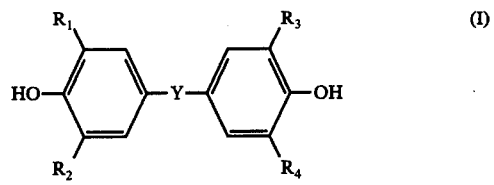

wherein Y represents an alkylene group containing 1 to 12 carbon atoms, —O—, —S—,

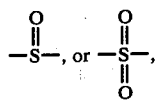

and $R_1$, $R_2$, $R_3$ and $R_4$, independently from each other, represent a hydrogen atom, an alkyl group containing 1 to 3 carbon atoms, a chlorine atom, or a bromine atom.

4,4'-Dihydroxydiphenyl-2,2-propane (bisphenol A) is an especially preferred dihydroxy compound used in this invention.

The aqueous alkali solution used in this invention is an aqueous solution of a strongly basic hydroxide such as sodium hydroxide or potassium hydroxide. The use of an aqueous solution of sodium hydroxide is especially preferred. The concentration of the basic hydroxide in the aqueous alkali solution is usually 5 to 10% by weight. The amount of the basic hydroxide is preferably in slight excess of 2 moles which is the stoichiometrically required amount of the dihydroxy compound. Specifically, the preferred amount of the basic hydroxide is 2.2 to 3.0 moles per mole of the dihydroxy compound.

The process of this invention is characterized in that a polycarbonate oligomer is produced by a two-stage reaction in which a first-stage reaction is carried out in a tubular reactor and a second-stage reaction, in a tank-type reactor. The first-stage reaction is performed by contacting a mixture of a dihydroxy compound and an aqueous alkali solution with phosgene in the presence of an organic solvent in a tubular reactor. The first-stage reaction consists mainly of a reaction of converting one or two of the two hydroxyl groups of the dihydroxy compound to —OCOCl by phosgenation. In the case of using bisphenol A, this reaction is schematically shown as follows:

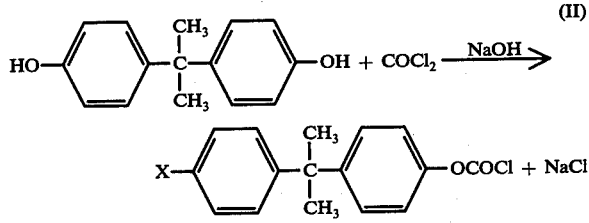

wherein X represents —OH, —ONa or —OCOCl.

The second-stage reaction carried out in a tank-type reactor consists mainly of a reaction of forming a polycarbonate oligomers of a relatively low molecular weight, say, 2 to 20 as the degree of polymerization by the condensation reaction of the phosgenation reaction product. An example of forming a dimer (degree of polymerization = 2) is schematically shown as follows:

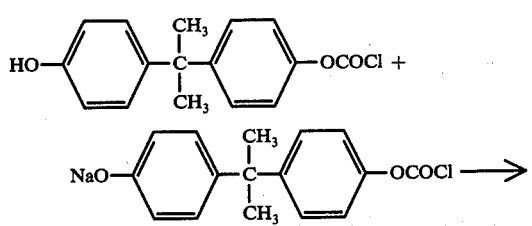

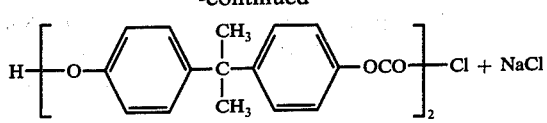

The polycarbonate oligomer formed in the tank-type reactor may be converted to a polycarbonate having a high molecular weight, say, 20 to 100 as the degree of polymerization by introducing it into a polymerization reactor, and subjecting it to the same condensation reaction as shown by formula (III) in the presence of a polymerization catalyst.

The first-stage reaction in the present invention which is carried out in the tubular reactor is directed mainly to the production of a phosgenation reaction product having a degree of polymerization of 1. The first-stage reaction product, however, may contain the unreacted dihydroxy compound or a small amount of a polycarbonate oligomer of a very low molecular weight expressed by the degree of polymerization of 2 or 3, or both of these compounds.

On the other hand, the second-stage reaction carried out in the tank-type reactor is directed mainly to the formation of a polycarbonate oligomer having a degree of polymerization of 2 to 20. The second-stage reaction may partly involve the phosgenation of the unreacted dihydroxy compound, or a reaction of forming a polycarbonate having a degree of polymerization of slightly more than 20, or both of these reactions.

It is necessary that the dihydroxy compound and the aqueous alkali solution used in the first-stage reaction should be mixed before they contact phosgene, or an organic solvent, or both in a tubular reactor. This mixing usually causes a greater part of the dihydroxy compound to dissolve in the aqueous alkali solution. It is generally preferred, but not always necessary, to dissolve the dihydroxy compound completely in the aqueous alkali solution. Mixing of the dihydroxy compound with the aqueous alkali solution is performed preferably at a temperature of 10° to 30° C. in view of the solubility of the dihydroxy compound, the oxidative degradation of the dihydroxy compound, the removal of the heat of reaction, etc. It is also preferred to maintain the mixture at this temperature during feeding into the tubular reactor. As needed, an antioxidant such as sodium hydrosulfite may be added to the mixture of the dihydroxy compound and the aqueous alkali solution or to the tubular or tank-type reactor in order to prevent the the oxidative degradation of the dihydroxy compound.

Phosgene used in the process of this invention may be fed in the liquid or gaseous state. It may be fed singly, but preferably, it is mixed with the organic solvent before contact with the aqueous alkali solution. When phosgene is mixed with the organic solvent, it is preferred that the solvent be cooled to about −10° C. to +20° C. and the solution of phosgene at this temperature be fed into the tubular reactor, in order to increase the absorption of phosgene and to remove the heat of reaction.

The organic solvent used in this invention is inert to the reactions, and dissolves the polycarbonate oligomer formed and a high-molecular-weight polycarbonate obtained by polymerizing it. Examples of the organic solvent are chlorinated hydrocarbons such as methylene chloride, tetrachloroethane, 1,2-dichloroethylane, chloroform, trichloroethane, dichloroethane or chlorobenzene, dioxane, tetrahydrofuran, and acetophenone. They are used either alone or as mixture. The preferred amount of the solvent is such that the concentration of the polycarbonate oligomer in the solution is 10 to 30% by weight. Preferably, the volume ratio of the organic solvent (organic layer) to the alkaline aqueous solution of the dihydroxy compound (aqueous layer) is 0.2–1.0.

Figure 2:
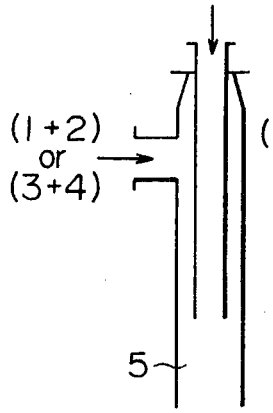

One procedure for feeding the mixture of the dihydroxy compound and the aqueous alkali solution, phosgene and organic solvent into a tubular reactor in order to perform the first-stage reaction is shown in FIG. 2. The mixture of the dihydroxy compound and the aqueous alkali solution is fed into either an outside tube or an inside tube of a double tube of the structure shown in FIG. 2, and the phosgene and organic solvent are fed into the other. Thus, at the outlet portion of the double tube, the mixture of the dihydroxy compound and the aqueous alkali solution is contacted with phosgene in the presence of the organic solvent to perform the first-stage reaction. When a double tube of the structure shown in FIG. 2 is used, there is no particular limitation on the diameter of the inside and outside tubes, but it should preferably be so designed that the linear velocities of solutions flowing through the inside and outside tubes are equal to each other.

Figure 3:
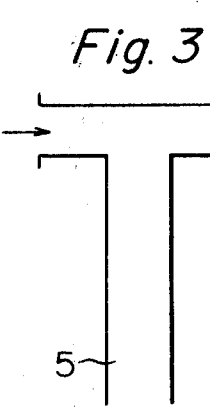

Another procedure for feeding starting substances into a tubular reactor in order to perform the first-stage reaction comprises using a T-shaped tube having two feed openings as shown in FIG. 3, and feeding the mixture of the dihydroxy compound and the aqueous alkali solution, and the mixed solution of the organic solvent and phosgene into the feed openings separately.

Figure 4:
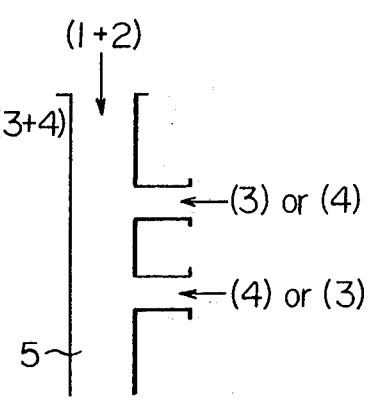

Alternatively, a tube having three feed openings as shown in FIG. 4 may be used, and the mixture of the dihydroxy compound and the aqueous alkali solution, phosgene, and the organic solvent are separately fed into the tube from these openings to perform the first-stage reaction in the tube.

In this way, the mixture of the dihydroxy compound and the aqueous alkali solution may be contacted with phosgene in the presence of the organic solvent into a tubular rector in accordance with various modified embodiments by selecting the structure of the tubular reactor. The structures shown in FIGS. 2, 3 and 4 are merely typical examples, and do not limit the process of this invention.

Preferably, the outlet portions of these feed tubes are coated with polytetrafluoroethylene or lined with glass, or are made of stainless steel.

In order to perform more uniform contacting of the mixture of the dihydroxy compound and the aqueous alkali solution with phosgene and organic solvent in the first-stage reaction, a static mixing device such as a static mixer may be provided at those parts in which the contacting is performed. This renders the first-stage reaction more efficient. Furthermore, two or more tubular reactors may be used, as needed, in performing the contacting.

It is preferred that the reaction time in the first stage reaction be generally 0.5 to 15 seconds. If the reaction time is less than 0.5 second, phosgenation sometimes does not proceed sufficiently. When it exceeds 15 seconds, heat is generated by local reactions, and side-reactions tend to be induced.

The first-stage reaction mixture formed in the tubular reactor is then introduced into a stirrer-equipped tank-type reactor filled with the second-stage reaction mixture, and consequently, the first-stage reaction mixture is mixed with the second-stage reaction mixture with stirring. The second-stage reaction mixture in the tank-type reactor is the one formed by the second-stage reaction of the first-stage reaction mixture introduced into the tank-type reactor. It consists of a solution of the polycarbonate oligomer formed by the second-stage reaction in the organic solvent (organic layer), and the aqueous alkaline solution (aqueous layer). The organic layer and the aqueous layer are maintained in the mixed stage by stirring so that they do not separate as two distinct layers. The phosgenation product having a degree of polymerization of 1 formed in the tubular reactor undergoes the second-stage reaction while it is mixed with the second-stage reaction mixture. Thus, it is converted to a polycarbonate oligomer having a degree of polymerization of at least 2.

In order to obtain good results in the process of this invention, it is important to maintain the reaction temperature in the tank-type reactor at a predetermined point, and the temperature of the reaction solution is desirably controlled within the range of ±3° C. with regard to the predetermined temperature. The reaction temperature in the tank-type reactor differs according to the kind of the organic solvent used, but should be those which are below the boiling point of the solvent and can inhibit side-reactions. For example, when methylene chloride is used as the solvent, the preferred reaction temperature is about 15 to 30° C.

In order to maintain the reaction temperature in the tank-type reactor at a predetermined point, it is necessary to remove the heat of reaction sufficiently. For this purpose, the reaction mixture in the tank-type reactor is cooled by various methods, for example by the provision of an externally cooling jacket in the reactor, or the provision of a coil-like cooling tube inside the reactor, or by circulating the reaction mixture in the tank-type reactor and providing a heat-exchanger in the circulating path. There is no particular limitation on a circulating pump for circulating the reaction mixture, and it may be any desired type. The heat-exchanger may be of any known type. Desirably, however, the heat-exchanger is one which undergoes little hold-up, and can have a large heat-transmitting area and a high overall heat transmission coefficient. The flow rate of the reaction mixture to be circulated is not limited in particular, and can be any desired value selected according to the capacity of the heat-exchanger. It is necessary however that the reaction mixture should be circulated at a linear velocity sufficient to prevent the separation of it into an organic layer and an aqueous layer. Generally, the preferred average number of circulating cycles (defined as the ratio of the flow rate circulated to the flow rate of the first-stage reaction product fed into the tank-type reactor) is 2 to 30.

The average residence time of the reaction mixture in the tank-type reactor is preferably 5 to 20 minutes.

The tubular reactor for the first-stage reaction may be connected in any desired manner to the tank-type reactor for the second-stage reaction. Preferably, the outlet of the tubular reactor is inserted in the tank-type reactor.

The inside wall of the tubular reactor and the tank-type reactor are preferably coated with polytetrafluoroethylene, lined with glass, or made of stainless steel.

The process of this invention is described specifically by the accompanying drawings.

FIG. 1 is a flowsheet showing one example of the performance of the process of this invention. In FIG. 1, 1 represents a feed of a dihydroxy compound; 2, a feed of an alkaline aqueous solution; 3, a feed of phosgene; and 4, a feed of an organic solvent. These feeds are mixed in a tubular reactor 5 to perform a first-stage reaction. FIGS. 2 to 4 show typical types of the structure of the outlet portion of feed pipes for these feeds. In these figures, (1+2) means that the dihydroxy compound and the aqueous alkaline solution are fed in the form of a mixture, and (3+4) means that the phosgene and organic solvent are fed in the form of a mixture. The outlet of the tubular reactor 5 is inserted in the reaction mixture accomodated in a tank-type reactor 6. The first-stage reaction product 7 flowing out from the tubular reactor 5 is mixed with the reaction mixture in the tank-type reactor 6. The reference numeral 8 represents a stirrer; 9, a cooling jacket; 10 and 11, an inlet and an outlet respectively for a cooling medium for the cooling jacket; 12, a pump for circulating the reaction mixture; 13, a heat-exchanger for cooling the reaction mixture, 14 and 15, an inlet and an outlet respectively for a cooling medium for a heat-exchanger; 16, the withdrawal of the reaction mixture by overflowing; and 17, withdrawal of the reaction mixture by the control of the liquid level.

As stated hereinabove, the process of this invention is characterized by connecting two types of reactors, a tubular reactor and a tank-type reactor, reacting a mixture of a dihydroxy compound and an aqueous alkali solution with phosgene in the presence of an organic solvent, adjusting the reaction time to a relatively short time so that the first-stage reaction in the tubular reactor consists substantially of the phosgenation of the dihydroxy compound, introducing the first-stage reaction product into a tank-type reactor, and subjecting it to the second-stage reaction with stirring at a predetermind reaction temperature while fully removing the heat of reaction so that the second-stage reaction consists substantially of the polycarbonate oligomer-frorming reaction by condensation, thus performing the phosgenation reaction of the dihydroxy compound and the oligomerization of the phosgenation product in substantially separate reaction zones.

Since the process of this invention can inhibit side reactions, the ratio of utilization of the reaction materials increases, and polycarbonate oligomers having very uniform superior quality can be obtained.

Polymerization of the polycarbonate oligomers obtained by the process of this invention can afford polycarbonates of high molecular weights. In the polymerization, a known chain terminating agent such as phenol or p-tert.butyl phenol, is used. Generally, the chain terminating agent is fed into a tubular reactor, or a polymerization reactor before adding a polymerization catalyst. The amount of the chain terminating agent is 1 to 5 mole % based on the dihydroxy compound. The polymerization catalyst is generally a tertiary amine typified by triethylamine or tributylamine, or its salt or quaternary ammonium salt.

According to the process of this invention described hereinabove, the loss of the starting materials is little, the conversion is high, and the reproducibility of the reaction is superior. Hence, polycarbonates prepared from the resulting polycarbonate oligomers have an extremely small amount of the unreacted compounds. Moreover, since the polymers have a low terminal chlorine content, and the dispersion of their molecular weight is little, their have good quality.

The following examples illustrate the process of the present invention in more detail.

EXAMPLE 1

A tubular reactor of the type shown in FIG. 2 which contained a double-structure feed tube coated with polytetrafluoroethylene was used. The inside tube had a diameter of 1 inch, and the outside tube had a diameter of 1.75 inches. The tubular reactor itself was also coated with polytetrafluoroethylene, and had a diameter of 1.75 inches and a length of 200 mm.

The tubular reactor was connected to a 40-liter glass-lined tank-type reactor in the manner shown in FIG. 1. The tank-type reactor was equipped with an externally circulating circuit for cooling the reaction mixture, and a multitube heat-exchanger was provided in the circulating circuit.

A mixed solution consisting of 4,4'-dihydroxydiphenyl-2,2-propane (flow rate 15.2 kg/hr), a 7% by weight aqueous solution of sodium hydroxide (flow rate 104.8 kg/hr) and sodium hydrosulfite (flow rate 20 g/hr) was fed at 20° to 25° C. into the outside tube of the double-structure feed tube, and a mixed solution of liquefied phosgene (flow rate 7.3 kg/hr) and methylene chloride (flow rate 66.5 kg/hr) was fed at 0° to 10° C. into the inside tube. The average residence time of the reaction mixture in the tubular reactor was 7 seconds.

The first-stage reaction product which left the tubular reactor was mixed with the reaction mixture accomodated in the tank-type reactor with stirring. The reaction mixture in the tank-type reactor was subjected to a second-stage reaction while it was circulated by a circulating pump at a flow rate of about 3500 liters/hr, thereby to afford a polycarbonate oligomer. The temperature of the reaction mixture in the tank-type reactor was maintained at about 20° C. by adjusting the amount of a cooling medium flowing into the heat-exchanger. The reaction mixture was withdrawn from the tank-type reactor by overflowing. The reaction mixture was tested, and the results are shown in Table 1.

The resulting polycarbonate oligomer was polymerized by a batchwise method and a continuous method described below.

Batchwise Polymerization Method

To 1 liter of the reaction mixture containing the polycarbonate oligomer, which was withdrawn from the tank-type reactor, was added 1.4 g of p-tert.butyl phenol as a chain terminating agent. They were vigorously stirred to an emulsified state. Then, 0.1 ml of triethylamine as a polymerization catalyst was added, and the batchwise polymerization was performed for 60 minutes.

Continuous Polymerization Method

A separate tank-type polymerization reactor was connected in cascade to the tank-type reactor used to perform the second-stage reaction. The polycarbonate oligomer-containing reaction mixture withdrawn from the tank-type reactor used to perform the second-stage reaction was introduced directly into the tank-type polymerization reactor. Separately, a solution of 1 kg of p-tert.butyl phenol in 6 liters of methylene chloride was fed into the tank-type polymerization reactor at a flow rate of 2 kg/hr. They were vigorously stirred, and a solution of 1 liter of triethylamine in 10 liters of methylene chloride was added at a flow rate of 0.12 kg/hr.

The continuous polymerization was performed for a total of 30 minutes.

The results of the two types of polymerization are shown in Table 2.

EXAMPLE 2

A polycarbonate oligomer was prepared under the same conditions as in Example 1 except that a plate-type heat-exchanger was used instead of the multitube heat-exchanger; the amount of circulation by the circulating pump was changed to about 1500 liters/hour; the withdrawal of the reaction mixture from the tank-type reactor was performed by controlling the liquid level instead of overflowing; and a solution of 1 kg of p-tert.butyl phenol in 6 liters of methylene chloride was fed into the tank-type reactor at a flow rate of 2.0 kg/hr. The results are shown in Table 1.

The resulting polycarbonate oligomer was continuously polymerized under conditions similar to those used in Example 1 (in order to maintain the correspondence of the polymerization conditions, the supply of a methylene chloride solution of p-tert.butyl phenol to the polymerization reactor was omitted in the continuous polymerization performed in Example 2). The results are shown in Table 2.

EXAMPLE 3

A polycarbonate oligomer was produced under the same conditions as in Example 1 except that the flow rates of the feeds were doubled as shown below; and a methylene chloride solution of p-tert.butyl phenol was fed into the tank-type reactor as in Example 2 (the concentration of this solution was the same as in Example 2, but its feed rate was 4.0 kg/hr, double the feed rate in Example 2).

| Feed | Flow rate |
| --- | --- |
| 4,4'-Dihydroxydiphenyl-2,2-propane | 30.4 kg/hr |
| 7% by weight aqueous solution of sodium hydroxide | 209.6 kg/hr |
| Sodium hydrosulfite | 40 g/hr |
| Liquefied phosgene | 14.6 kg/hr |
| Methylene chloride | 133 kg/hr |

In order to examine the reproducibility of the reaction, the reaction mixture was sampled three times at one-hour intervals in the above process. Samples obtained were designated A, B and C. These three samples were tested, and the results are shown in Table 1.

On the other hand, the polycarbonate oligomer was polymerized every one hour by a batch method and a continuous method under conditions similar to those used in Example 1 so that it corresponded the polymerization of the samples A, B and C respectively. The results obtained are shown in Table 2.

EXAMPLE 4

A polycarbonate oligomer was produced under the same conditions as in Example 1 except that the feed rates of the feeds were tripled. The results are shown in Table 1.

The polycarbonate oligomer obtained was continuously polymerized under conditions similar to those used in Example 1. The results are shown in Table 2.

EXAMPLE 5

A polycarbonate oligomer was produced under the same conditions as in Example 1 except that two tubular reactors equipped with a double-structure feed tube were used as connected in parallel to each other and inserted in the tank-type reactor, and the flow rate of each feed into the tubular reactor was increased to 1.5 times (namely, to 3 times in total). The results are shown in Table 1.

The polycarbonate oligomer was continuously polymerized under conditions similar to those in Example 1. The results are shown in Table 2.

COMPARATIVE EXAMPLE 1

Raschig rings were packed into a jacketed tubular reactor having an inside diameter of 10 cm and a length of 1.5 meters (L/D=15), and the various feeds used in Example 1 were fed into the reactor from its top at the same flow rates as in Example 1. While maintaining the temperature of the reaction mixture at 20° C., the reaction mixture was withdrawn from the bottom of the reactor, thereby to form a polycarbonate oligomer. In the above process, the reaction mixture was sampled three times at 1-hour intervals to obtain samples A, B and C.

The flow rates of the various feeds were increased to two times, and a polycarbonate oligomer was produced in the same way as described above. In this case, the temperature of the reaction mixture could not be maintained at 20° C., but rose to 27° C. at the outlet of the tubular reactor. The reaction mixture was sampled three times at 1-hour intervals to obtain samples D, E and F respectively.

Samples A to F were tested, and the results are shown in Table 1.

On the other hand, the polycarbonate oligomers of samples A, B, C, D, E, and F were each polymerized batchwise under conditions similar to those used in Example 1. The results are shown in Table 2.

COMPARATIVE EXAMPLE 2

In the reaction apparatus used in Example 5, two ordinary cylindrical feed tubes each having a diameter of 1 inch were inserted in the tank-type reactor instead of the tubular reactor having a double-structure feed tube.

The same mixed solution consisting of 4,4'-dihydroxydiphenyl-2,2-propane, a 7% by weight aqueous solution of sodium hydroxide and sodium hydrosulfite as used in Example 1 was fed into one of the feed tubes under the same conditions as in Example 1. On the other hand, the same mixed solution of liquefied phosgene and methylene chloride as used in Example 1 was fed into the other feed tube under the same conditions as in Example 1. Hence, the two mixed solutions did not contact each other in the tube, but did in the tank-type reactor. The reaction conditions in the tank-type reactor were the same as in Example 1. In this way, a polycarbonate oligomer was produced (Comparative Example 2-1). Polycarbonate oligomers were also produced under the same conditions as above except that the flow rates of the feeds were increased to 2 times and 3 times, respectively (Comparative Examples 2-2 and 2-3). The results of the three comparison runs are shown in Table 1.

On the other hand, the polycarbonate oligomers obtained in Comparative Examples 2-1, 2-2 and 2-3 were each continuously polymerized under similar conditions to those in Example 1. The results are shown in Table 2.

COMPARATIVE EXAMPLE 3

A polycarbonate was produced under the same conditions as in Example 2 except that the reaction mixture in the tank-type reactor was cooled by using a cooling jacket fitted to the tank-type reactor instead of using the plate-type heat-exchanger. The temperature of the reaction mixture in the tank-type reactor could be maintained at 20° C. However, when the feeds of the starting materials were increased to 2 times as in Example 3 and to 3 times as in Example 4, the removal of the heat of reaction by the cooling jacket alone was insufficient, and it was impossible to maintain the temperature of the reaction mixture in the tank-type reactor at 20° C.

Table 1

| Reaction of forming polycarbonate oligomers | | | | |
|---|---|---|---|---|
| Samples | Flow rates of feeds (*1) | Molecular weight of oligomer (*2) | Ratio of decomposition of phosgene (%) (*3) | Index of phosgene decomposition (*4) |
| Example 1 | 1 | 1100 | 10.2 | 74 |
| Example 2 | 1 | 1080 | 10.2 | 74 |
| Comparative Example 1-A | 1 | 620 | 10.5 | 77 |
| 1-B | 1 | 560 | 10.3 | 75 |
| 1-C | 1 | 700 | 10.5 | 77 |
| Comparative Example 2-1 | 1 | 1230 | 10.6 | 77 |
| Example 3-A | 2 | 1050 | 10.6 | 77 |
| 3-B | 2 | 1020 | 10.7 | 78 |
| 3-C | 2 | 1040 | 10.6 | 77 |
| Comparative Example 1-D | 2 | 450 | 11.5 | 84 |
| 1-E | 2 | 420 | 13.0 | 95 |
| 1-F | 2 | 500 | 12.7 | 93 |
| Comparative Example 2-2 | 2 | 1090 | 12.6 | 92 |
| Example 4 | 3 | 930 | 12.0 | 88 |
| Example 5 | 3 | 980 | 10.9 | 80 |
| Comparative Example 2-3 | 3 | 1010 | 13.7 | 100 |

(*1) The flow rates of the feeds in Example 1 were taken as 1.
(*2) The number average molecular weight measured by the vapor pressure equilibrium method.
(*3) The amount of phosgene which was consumed by a side-reaction is calculated from the amount of Na₂CO₃ formed in the aqueous layer. The decomposition ratio is defined as the percentage of this amount based on the amount initially charged.
(*4) The degree of phosgene decomposition is expressed by a proportional index. In Table 1, Comparative Example 2-3 in which the decomposition ratio of phosgene is the greatest is taken as a standard, and the decomposition index at this time is made 100. Smaller phosgene decomposition indices mean lesser degrees of side-reaction.

Table 2

| Reaction of polymerizing oligomers to polymers | | | | |
|---|---|---|---|---|
| Sample | Method of polymerization | Molecular weight ×10⁴ (*1) | Index of remaining NaOH in the aqueous phase (*2) | Ratio of unreacted monomer (%) |
| Example 1 | Batchwise | 2.5 | 100 | 0.6 |
|  | Continuous | 2.4 | 99 | 0.6 |
| Example 2 | Continuous | 2.5 | 90 | 0.4 |
| Comparative Example 1-A | Batchwise | 2.4 | 82 | 1.7 |
| 1-B | " | 2.5 | 91 | 0.3 |
| 1-C | " | 2.4 | 96 | 0.9 |
| Comparative Example 2-1 | Continuous | 2.5 | 99 | 0.8 |
| Example 3-A | Batchwise | 2.5 | 74 | 0.6 |
| 3-B | " | 2.5 | 71 | 0.8 |
| 3-C | " | 2.5 | 76 | 0.6 |
| Example 3-A | Continuous | 2.5 | 87 | 0.9 |
| 3-B | " | 2.4 | 81 | 1.0 |
| 3-C | " | 2.5 | 85 | 0.8 |
| Comparative Example 1-D | Batchwise | 2.4 | 51 | 1.7 |
| 1-E | " | 2.4 | 49 | 2.6 |
| 1-F | " | 2.3 | 30 | 3.5 |
| Comparative Example 2-2 | Continuous | 2.4 | 60 | 1.1 |
| Example 4 | Continuous | 2.4 | 56 | 1.2 |
| Example 5 | Continuous | 2.4 | 62 | 0.9 |
| Comparative Example 2-3 | Continuous | 2.4 | 41 | 2.6 |

(*1) The viscosity average molecular weight from a methylene chloride solution.
(*2) The concentration of NaOH remaining in the aqueous layer after polymerization is expressed by a proportional index. Example 1 in which the residual NaOH concentration is the highest is taken as a standard, and the residual indices at this time is expressed as 100. Higher residual indices mean lesser degrees of the decrease of sodium hydroxide by side-reaction both in the oligomer-forming reaction and in the polymerization reaction.

It is seen from the results shown in Tables 1 and 2 that the reproducibility of the reaction and the degree of side-reaction depend fairly greatly on the amounts of feed materials charged.

A comparative study shows that in the Examples of the invention, the occurrence of an undesirable side-reaction is reduced, fluctuations of reaction with passage of time are little and thus, the reproducibility of the reaction is good, and the conversion is high, as compared with the Comparative Examples. These differences between Examples and Comparative Examples are especially remarkable when the flow rates of the materials are increased.

Furthermore, the polycarbonate oligomer obtained by the process of this invention contains a well-balanced terminal groups which can inhibit its decomposition at the time of polymerization. Thus, a polycarbonate obtained by polymerizing the polycarbonate oligomer has good reproducibility of quality, and the yield of the polymer is high.

What we claim is:

1. A process for producing polycarbonate oligomers by the reaction of dihydroxy compounds with phosgene, which comprises contacting a mixture of a dihydroxy compound and an aqueous alkali solution with phosgene in the presence of an organic solvent in a tubular reactor to perform a first-stage reaction wherein the reaction time is from 0.5 to 15 seconds, introducing the first-stage reaction mixture into a tank-type reactor equipped with a stirrer and containing the aqueous alkali solution and a solution in the organic solvent of a polycarbonate oligomer formed by the reaction of the first-stage reaction product in a second stage, and performing the second-stage reaction, wherein the reaction time is from 5 to 20 minutes, while stirring the reaction mixture in the tank-type reactor and maintaining it at a predetermined temperature by sufficient removal of the heat of reaction.

2. The process of claim 1 wherein the dihydroxy compound is at least one compound of the formula

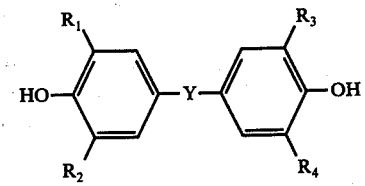

wherein Y represents an alkylene group containing 1 to 12 carbon atoms, —O—, —S—,

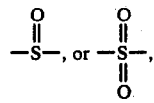

and $R_1$, $R_2$, $R_3$ and $R_4$, independently from each other, represent a hydrogen atom, an alkyl group containing 1 to 3 carbon atoms, a chlorine atom or a bromine atom.

3. The process of claim 1 wherein the aqueous alkali solution is a 5–10% by weight aqueous solution of a basic hydroxide selected from the group consisting of sodium hydroxide and potassium hydroxide, the basic hydroxide being used in an amount of 2.2 to 3.0 moles per mole of the dihydroxy compound.

4. The process of claim 1 wherein the organic solvent is an organic solvent which is inert to the reaction and can dissolve the polycarbonate oligomer and a polycarbonate obtained by polymerizing it.

5. The process of claim 1 wherein a mixture at 10° to 30° C. of the dihydroxy compound and the aqueous alkali solution and a solution at −10° to +20° C. of the phosgene in the organic solvent are fed into the tubular reactor.

* * * * *